(12) United States Patent
Choy

(10) Patent No.: US 6,846,284 B2
(45) Date of Patent: *Jan. 25, 2005

(54) METHOD AND APPARATUS FOR TREATMENT OF MONO-FREQUENCY TINNITUS

(75) Inventor: Daniel S. J. Choy, New York, NY (US)

(73) Assignee: Tinnitus Control, Inc., New York, NY (US)

( * ) Notice: Subject to any disclaimer, the term of this patent is extended or adjusted under 35 U.S.C. 154(b) by 48 days.

This patent is subject to a terminal disclaimer.

(21) Appl. No.: 10/319,281

(22) Filed: Dec. 12, 2002

(65) Prior Publication Data

US 2003/0114728 A1 Jun. 19, 2003

Related U.S. Application Data

(60) Provisional application No. 60/340,271, filed on Dec. 18, 2001.

(51) Int. Cl.[7] ............................. A61M 21/00; A61B 5/00
(52) U.S. Cl. .......................................... 600/28; 600/559
(58) Field of Search ................................. 128/897, 107, 128/748; 600/28, 559, 27, 25, 26; 601/46–48, 2, 78–8; 607/55, 56, 136, 137; 381/68–68.3, 73.1, 83; 604/36

(56) References Cited

U.S. PATENT DOCUMENTS

| | | | |
|---|---|---|---|
| 4,222,393 A | * | 9/1980 | Hocks et al. ............... 600/559 |
| 5,325,872 A | * | 7/1994 | Westermann ............... 128/897 |
| 5,403,262 A | | 4/1995 | Gooch |
| 5,795,287 A | | 8/1998 | Ball et al. |
| 6,210,321 B1 | | 4/2001 | Di Mino et al. |
| 6,377,693 B1 | | 4/2002 | Lippa et al. |
| 6,610,019 B2 | * | 8/2003 | Choy ........................... 600/559 |
| 2002/0177877 A1 | | 11/2002 | Choy |
| 2004/0059251 A1 | * | 3/2004 | Choy ........................... 600/559 |

FOREIGN PATENT DOCUMENTS

| | | |
|---|---|---|
| DE | 10128642 A1 | 6/2001 |
| GB | 2134689 A | 8/1984 |
| WO | WO-03-051179 A2 | 6/2003 |

* cited by examiner

Primary Examiner—Samuel G. Gilbert
Assistant Examiner—Nikita R. Veniaminov
(74) Attorney, Agent, or Firm—Steven L. Nichols; Paul W. Fish; Rader, Fishman & Grauer PLLC

(57) ABSTRACT

Reciprocal noise cancellation of a patient's mono-frequency tinnitus tone is achieved utilizing an externally generated tone which is subjectively defined by a mono-frequency tinnitus patient to match his/her tinnitus tone in frequency and amplitude. An externally generated sound wave, selectively designated by subjective observations of a patient to match the patient's tinnitus tone is first applied to the tinnitus patient via earphones or a speaker system and then the same externally generated sound wave is sequentially phase shifted through a plurality of angularly shifted sequence steps to shift or slide the external sound wave through at least a 180 degree phase shift of the generated signal as it is applied to the patient to achieve a series of reductions of the patient's tinnitus tone and in one of such shifted steps a reciprocal, canceling relationship with the patient's tinnitus tone. The tinnitus treatment sequence of an externally generated sound wave and then the phase shifted externally generated tone achieve cancellation of the tinnitus tone of the patient as the sequential steps of the generated tone in effect slide across the tinnitus sound wave resulting in cancellation of the tinnitus tone. By replaying the sequential phase shifted segments of the patient treatment process a patient may utilize the previously recorded sequences in a patient self-treatment process.

24 Claims, 9 Drawing Sheets

METHOD AND APPARATUS FOR TREATMENT OF MONO-FREQUENCY TINNITUS

CROSS-REFERENCE TO RELATED U.S. APPLICATIONS

This application claims the benefit of the earlier filing date of U.S. Provisional Application No. 60/340,271, filed Dec. 18, 2001 and further relates to U.S. application Ser. No. 10/083,088 filed Mar. 1, 2002. The specification and disclosure of both of these related Applications are incorporated herein in their entirety by this reference.

TECHNICAL FIELD

The present inventions relate to the treatment of tinnitus patients and more particularly to improved clinical methods and apparatus for treatment of mono-frequency tinnitus patients utilizing phase shift cancellation principles.

BACKGROUND

Tinnitus is defined as the perception of sound by an individual when no external sound is present, and often takes the form of a hissing, ringing, roaring, chirping or clicking sound which may be intermittent or constant. According to the American Tinnitus Association, tinnitus afflicts more than 50 million Americans, and more than 12 million of those suffer so severely from tinnitus that they seek medical attention and many cannot function normally on a day-to-day basis.

Tinnitus, often referred to as ringing in the ears, is estimated to be present in approximately 50% of the US population over 65 years of age. In general, tinnitus takes many and varied forms, which may be related to its underlying cause. Tinnitus may be caused by, or related to, such diverse factors as trauma, drugs, hearing loss, the normal aging process or other unknown causes.

Previous approaches to treating tinnitus have focused on masking the tinnitus noise experienced by patients. While previous masking techniques have been unable to alleviate the problems of tinnitus patients, significant research has been done. In reporting on studies at the Oregon Tinnitus Clinic, Jack Vernon, director of the Oregon Hearing Research Center, stated that, in patient tinnitus studies, phase and tone relationships are of obvious and critical importance in tone masking of tinnitus. Vernon goes on to observe that one cannot repress the idea of canceling tinnitus by a proper phase adjustment of the external tone used in masking.

In commenting on Wegel's earlier tinnitus treatment findings that a slight mistuning of a masking external tone produced a beat-like sensation with the tinnitus sound, Vernon reported that, in a 100 patient study, he was able to detect a slight beat-like sensation in only four instances. Vernon therefore concluded that the beat-like sensation found by Wegel was most probably due to octave confusion resulting from Wegel not using a single pure tone, but rather a narrow band of noise. In conclusion, Vernon observed that phase manipulation justifies further patient studies as a masking parameter for tonal tinnitus treatments. Vernon's report on possible phase manipulation for treating tinnitus patients remained unchanged from its original publication in 1991 and as included in the 1997 edition of Shulman's treatise entitled "Tinnitus Diagnosis and Treatment."

In his above-referenced U.S. Application, Dr. Choy reports on favorable patient data from blind clinical studies utilizing a 180-degree phase shift of an externally generated tinnitus tone. More than 79% of patients studied reported either elimination of, or substantial reduction in the level of, tinnitus noise.

Neither current medical procedures nor electronic or sonic instrumentation permit or facilitate an objective determination of either the frequency or amplitude of the tinnitus noise a patient experiences. It is also not possible to subjectively determine an instantaneous phase of a point on a patient's virtual mono-frequency tinnitus tone.

This current state of tinnitus treatment has been bothersome for the tinnitus patient because the current state of medical knowledge and acoustic/electronics instrumentation does not yet permit one to objectively determine at what point on a patient's virtual endogenous tinnitus sound wave tinnitus tone (sine wave) an exogenous phase-shifted sine wave would be inserted in an attempt to cancel the patient's virtual tinnitus noise.

SUMMARY

In one of many possible embodiments of the present invention, reciprocal noise cancellation of a patient's mono-frequency tinnitus tone is achieved utilizing an externally generated tone which is subjectively defined by a mono-frequency tinnitus patient to match his/her tinnitus tone in frequency and amplitude. In accordance with one aspect of applicant's novel apparatus and process, an externally generated sound wave, selectively designated by subjective observations of a patient to match the patient's tinnitus tone is first applied to the tinnitus patient via earphones or a speaker system. Then, the same externally generated sound wave is sequentially phase shifted through a plurality of angularly shifted sequence steps to shift or slide the external sound wave through at least a 180 degree phase shift of the generated signal as it is applied to the patient to achieve in one of such shifted steps a reciprocal canceling relationship with the patient's tinnitus tone. The tinnitus treatment sequence of an externally generated sound wave and then the phase shifted externally generated tone achieve cancellation of the tinnitus tone of the patient as the sequential steps of the generated tone in effect slide across the tinnitus sound wave resulting in cancellation of the tinnitus tone.

In another exemplary embodiment, an improved apparatus for treating mono-frequency tinnitus patients includes a sound generator having selectable frequency and amplitude output wave controls, and an amplifier for audibly applying the output of the sound generator to a tinnitus patient whereby the patient subjectively defines his/her tinnitus tone in terms of frequency and amplitude. A phase shift network then incrementally shifts the generated output wave subjectively selected by a patient to match the patient's tinnitus tone and amplitude to thereby achieve sound cancellation of the patient's tinnitus tone by selectively shifting the generated output wave form through a plurality of incremental segments totaling a 180 phase shift relative to a predetermined starting point of the generated wave.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

To remedy the current deficiencies in diagnosing and treating tinnitus patients, and more particularly mono-frequency (single tone) tinnitus, applicant has developed a new, more efficient phase cancellation treatment process and apparatus that overcomes many of the shortcomings in the prior art. There is a long-felt need for an effective treatment for mono-frequency tinnitus patients to substantially reduce, relieve or eliminate the often substantially debilitating condition of tonal tinnitus.

Figure 1:
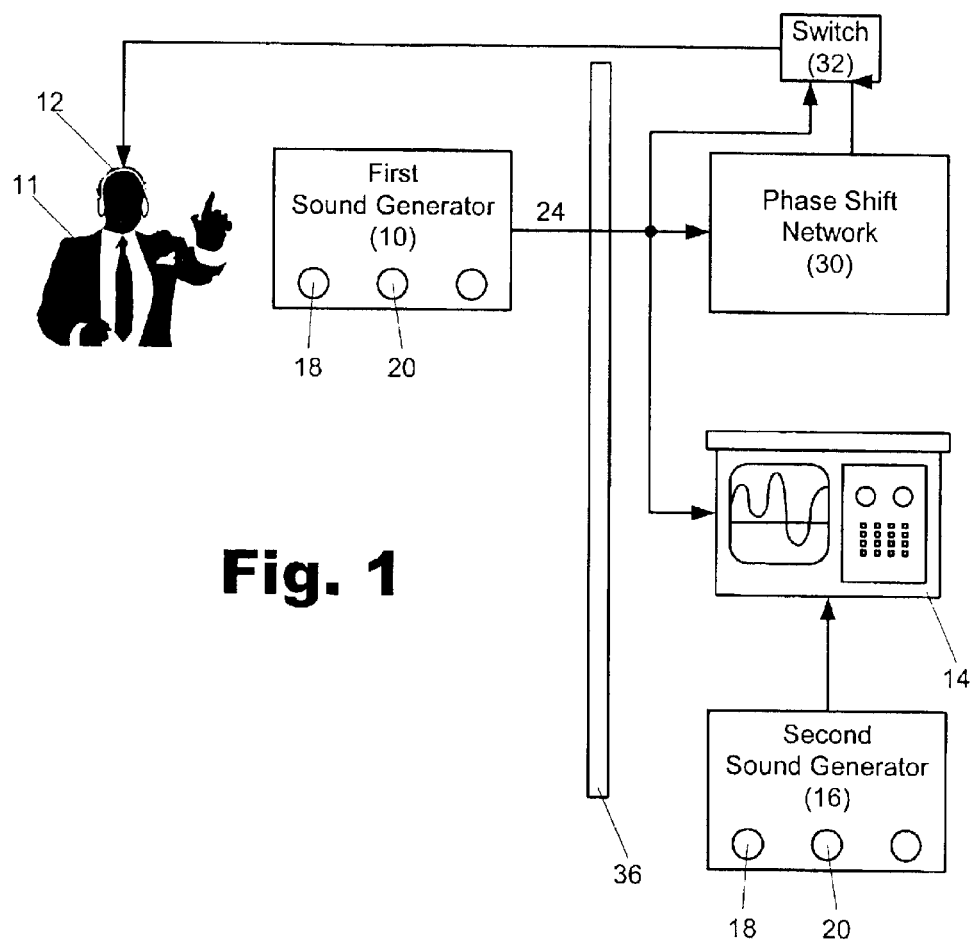
FIG. 1 is a block diagram of mono-frequency tinnitus treatment apparatus in accordance with an embodiment of the present invention.
Figure 2A:
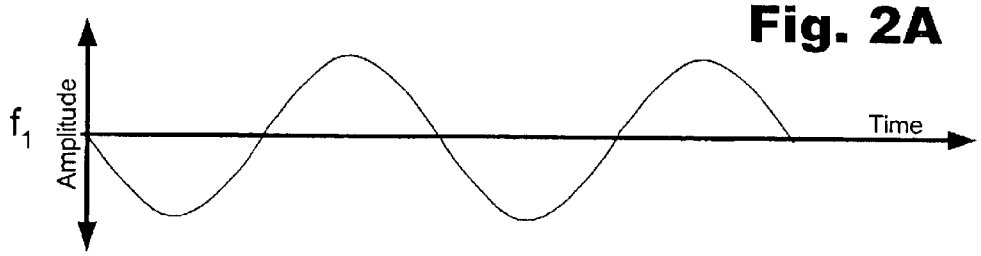
FIGS. 2A, 2B, 2C, 2D and 2E are a series of sine waves that graphically illustrate phase shift cancellation principles in accordance with embodiments of the present invention.
Figure 2B:
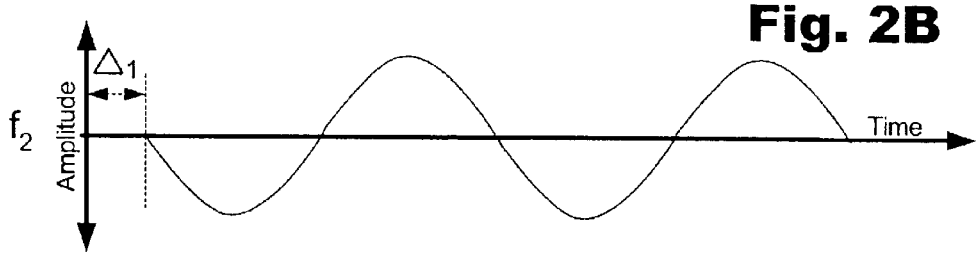
Figure 2C:
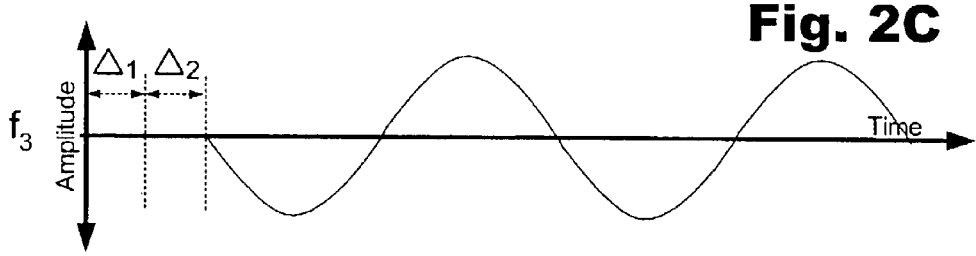
Figure 2D:
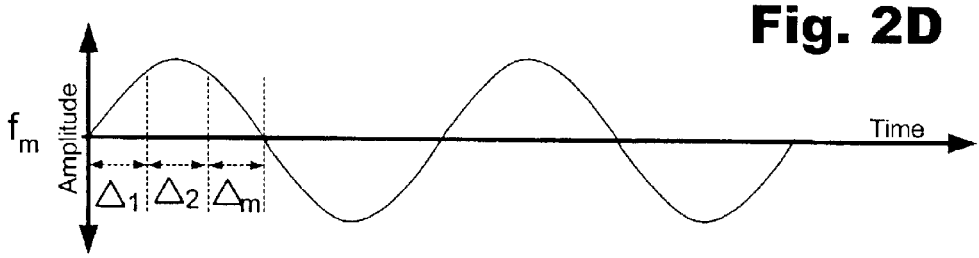
Figure 2E:
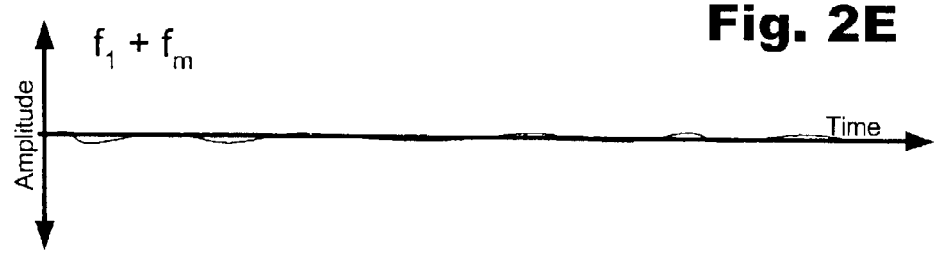

Referring now to FIG. 1, a preferred embodiment of a phase shift treatment system for mono-frequency tinnitus patients is illustrated in block diagram form. A sound generator 10, for example, an Agilent model 33120A function generator or any equivalent commercially available wave form generator, is coupled to a patient's headset 12 and to an input of an oscilloscope 14 which may, for example, be of the type commercially available in the U.S. from Tektronics, Inc. A second sound generator 16 is also coupled to another input of oscilloscope 14.

Sound generator 10 has a plurality of adjustable knobs, 18 and 20, and an output terminal 24. As will be hereinafter explained in further detail particularly with respect to FIG. 3, a mono-frequency tinnitus patient 11 is asked to adjust the frequency and amplitude of an audio signal generated by the sound generator 10 using, respectively, knobs 18 and 20, until the output of the sound generator applied to headphones 12 matches the tinnitus mono-frequency tone heard by the patient.

This subjective "sound-typing" is preferably repeated a plurality of times on a blind basis, i.e. the patient cannot see the oscilloscope 14. A barrier 36 may be placed between the patient 11 and the oscilloscope 14 and the sound generator 10. Additionally, either this is no display on the sound generator 10 that a patient 11 can observe, or any such display is masked and concealed from the patient 11. In this manner, if the patient is able to subjectively select roughly the same parameters a number of times to match his or her perceived tinnitus noise with the sound generator 10, there can be confidence that the output of the sound generator 10 accurately approximates the tinnitus noise experienced by the patient 11.

The subjective sound typing data for each of the self-typing steps is preferably recorded by an attending audiologist or physician. Additionally, the output of the first sound generator 10 can be matched by adjusting a second sound generator 16 to produce the same output. The outputs of the first sound generator 10 and the second sound generator 16 can be compared on the oscilloscope 14 to ensure they are the same. The output of the second sound generator 16 can be used, as will be described below, to prepare a treatment recording for the patient 11.

The principles of sound wave cancellation operate by superimposing, e.g. summing, a second sine wave having the same frequency and amplitude, as the first sine wave with a phase shift of 180 degrees. Sound wave cancellation is well understood in the electrical and measurement arts and is utilized in many technical fields including audiology, mechanics and electronics generally. With mono-frequency tinnitus, the patient should be able to adjust the output of the first sound generator 10 to approximate the tinnitus noise that he or she hears.

The method of accomplishing the phase shift cancellation effect of summing two waves of the same frequency and amplitude, but without any knowledge of the phase relationship of the first wave to the second wave relative to a common point, can be illustrated as follows. Sound generator 10 is set to a first tone having a frequency of $f_1$ and an amplitude of A (for example in milli-volts as displayed on sound generator 10) and connected to the first input of multi-beam oscilloscope 14. A second generator 16 is also set to the same tone with a like amplitude and the output is connected as a second input to oscilloscope 14.

With reference to FIGS. 2A–2E, it may be seen that by adjusting the phase of sine wave f through a series of steps, illustrated as $f_1 \ldots f_m$, the sum of $f_1$ plus $f_m$ (FIG. 2E) neutralizes or cancels the original signal $f_1$. As illustrated, $f_1$ plus $f_m$ cancel when $f_m$ is 180 degrees out of phase with $f_1$. Unfortunately for tinnitus patients, the structure and operation of the human auditory system is much more complex than the simple addition of two tonal sound waves as illustrated above on a multi-trace oscilloscope 14.

It is well understood in the field of audiology that humans and animals can determine, to a considerable degree of precision, the direction of a sound wave remote from them and to some extent can also estimate the distance of a sound source. Numerous experiments in the field of audiology have attempted to analyze the mechanics by which so-called binaural localization is accomplished in humans and animals. There are two primary factors which assist one in determining the direction of an arriving sound: (1) relative intensity in the hearer's two ears and (2) the difference in phase between the ears or, for a sinusoidal tone, the difference in phase between the sound waves arriving at the right and left ear of the hearer respectively. Thus, it is clear that a human or animal auditory system can distinguish phase shifts of complex sound generally and for pure or mono-frequency tones specifically. This type of auditory analysis is frequency dependent and, for frequencies above 1 Khz, most observers tend to determine the direction of a sound source from the side of the ear receiving the louder sound. Thus in general, it appears that auditory localization by phase difference is most definite for a band of frequencies in the order of a few kilohertz. As discussed hereinafter, with reference to FIG. 3, in implementing tinnitus treatments, it is important to determine not only the tonal quality of the tinnitus signal but whether the tinnitus patient hears his/her tinnitus in both ears, in only one ear or, as many indicate when asked where they hear the tinnitus, in their head without reference to either ear.

Referring again to FIG. 1, the structure and operation of applicant's preferred embodiment of apparatus for treating mono-frequency tinnitus patients will be further described. A phase shift network 30 may be of any type known to those skilled in the auditory and electrical arts for applying a desired phase shift to the output of the first sound generator 10. Alternatively, the sound generator 10 may incorporate an output wave form phase shift feature. To select the wave form phase shift feature, an operator may dial in the desired phase shift (scaled in degrees), e.g. 10 degrees, 20 degrees etc. which affects the desired shifts, e.g. of $\Delta_1$, $\Delta_2$, etc. as shown in FIG. 2 or an appropriate automatic switching arrangement may be used.

As shown in FIG. 1, a switch 32 can selectively send the output of the first sound generator 10 to the patient's headphones 12. In an alternate position, the switch 32 sends the output of the phase shift network, i.e., the signal from the first sound generator 10 plus a phase shift, to the patient's headphones 12. If the sound generator 10 does not have a phase shift feature, the separate phase shift network 30 is utilized. The headphones 12 are preferably a high quality headset commercially available from, for example, Bose, Inc. of Massachusetts, U.S.A., under the trademark Quiet-Comfort.

Switch 32, as illustrated, applies the shifted output of the sound generator 10 to the headphones 12. The successively phase-shifted increments of sine wave tone from generator 10, as explained above, are successively generated relative to $f_1$, as illustrated in FIG. 2, to accomplish the reciprocal 180 degree phase canceling relationship through the steps illustrated as $f_2, f_3, \ldots f_m$.

Figure 3A:
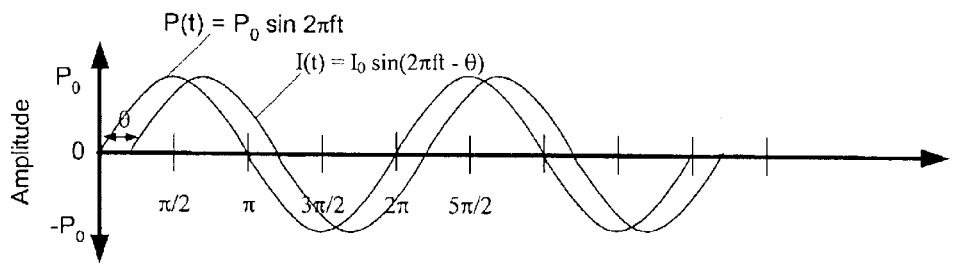
FIGS. 3A, 3B and 3C graphically illustrate the summation and cancellation for an assumed patient tinnitus wave form and an externally generated wave form having an arbitrary assumed offset of θ degrees in accordance with embodiments of the present invention.

Referring now to FIG. 3A, there is shown a theoretical graphical representation of the summing of a patient's tinnitus tone P(t) and an externally generated tone I(t) along with their respective mathematical equation representations. As stated above, the patient's tinnitus tone P(t) cannot be measured with existing electronic or sonic instrumentation, but, for convenience of discussion and analysis, it is illustrated as a sine wave of a particular frequency f(t). The respective wave forms for a patient's tinnitus tone P(t) and the generated wave form I(t) are based, as explained above, on the patient self-typing of his/her tinnitus tone as compared to the output of a sound generator 10, as explained in connection with FIG. 1.

Figure 3B:
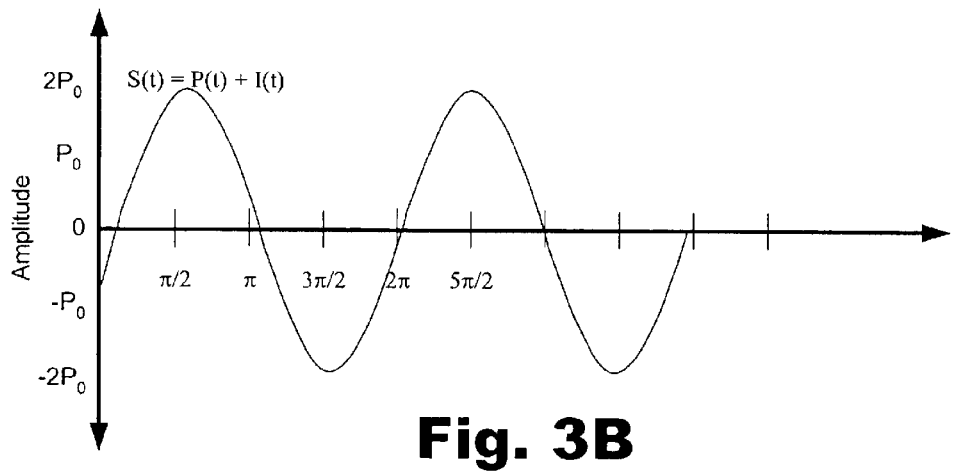
Figure 3C:
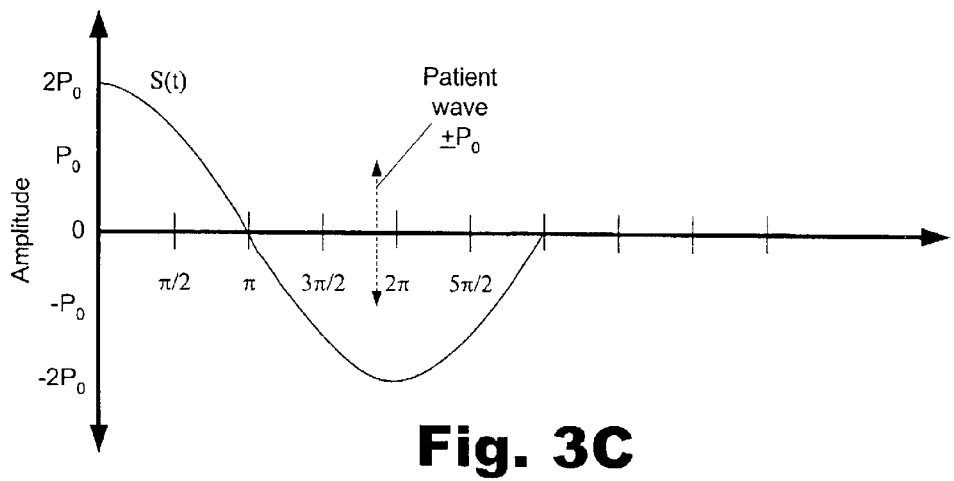

FIG. 3B illustrates a single sine wave representing the sum S(t) of P(t) and I(t) with the initial offset or separation angle θ as shown in FIG. 3A. The sum is expressed by its mathematical equivalent S(t). FIG. 3C illustrates the amplitude of a sine wave representing the arithmetic sum of the patient tinnitus wave P(t) and the input generated wave I(t). As illustrated in FIG. 3C the arithmetic sum S(t) of the two offset wave forms P(t) and I(t) having the aforementioned angular offset θ has an instantaneous amplitude less than the patient's tinnitus tone sound wave due to the cancellation effected by the offset phase shift angle θ which results in a diminution or cancellation of the patient's tinnitus tone as illustrated between the $2\pi/3$ to the $4\pi/3$ degree points on the sum S(t) wave form. Thus for approximately one-third of the 360 degree scale illustrated, partial cancellation occurs. By incrementally shifting the external tinnitus treatment tone I(t), we can theoretically nullify or completely cancel the patient's tinnitus tone P(t) when the input treatment tone I(t) reaches the 180 degree out-of-phase position, as shown in FIG. 2, as it slides across the patient tinnitus tone P(t) as described above. For a more complete understanding of the diminution and cancellation of a theoretical patient's tinnitus tone, reference may be had to FIGS. 3A, 3B and 3C and the following mathematical definitions and equations relating thereto:

Patient Sine Wave:

$$P(t) = P_0 \sin 2\pi f t$$

Where $P_0$ is amplitude, f is frequency and t is time.
Input Sine Wave from Generator:

$$I(t) = I_0 \sin(2\pi f t - \theta)$$

Where θ is the phase shift between P(t) and I(t) in radians. π radians=180°, 2π=360°.
Sum of P(t) and I(t):

$$S(t) = P(t) + I(t) = (P_0 \sin 2\pi f t) + I_0 \sin(2\pi f t - \theta)$$

Assume that $P_0 = I_0$, then $$S(t) = P_0[\sin 2\pi t + \sin(2\pi f t - \theta)] = [2P_0 \cos(\tfrac{1}{2}\theta)] \cdot [\sin(2\pi f t - \tfrac{1}{2}\theta)] = A \sin(2\pi f t - \tfrac{1}{2}\theta)$$

where A is the amplitude of the sum wave.
Thus,
A=$2P_0 \cos(\tfrac{1}{2}\theta)$;
$\sin(2\pi f t - \tfrac{1}{2}\theta)$ is the sinusoidal variation of the sum wave; and
$\tfrac{1}{2}\theta$ is the phase shift of the sum wave.

Figure 4:
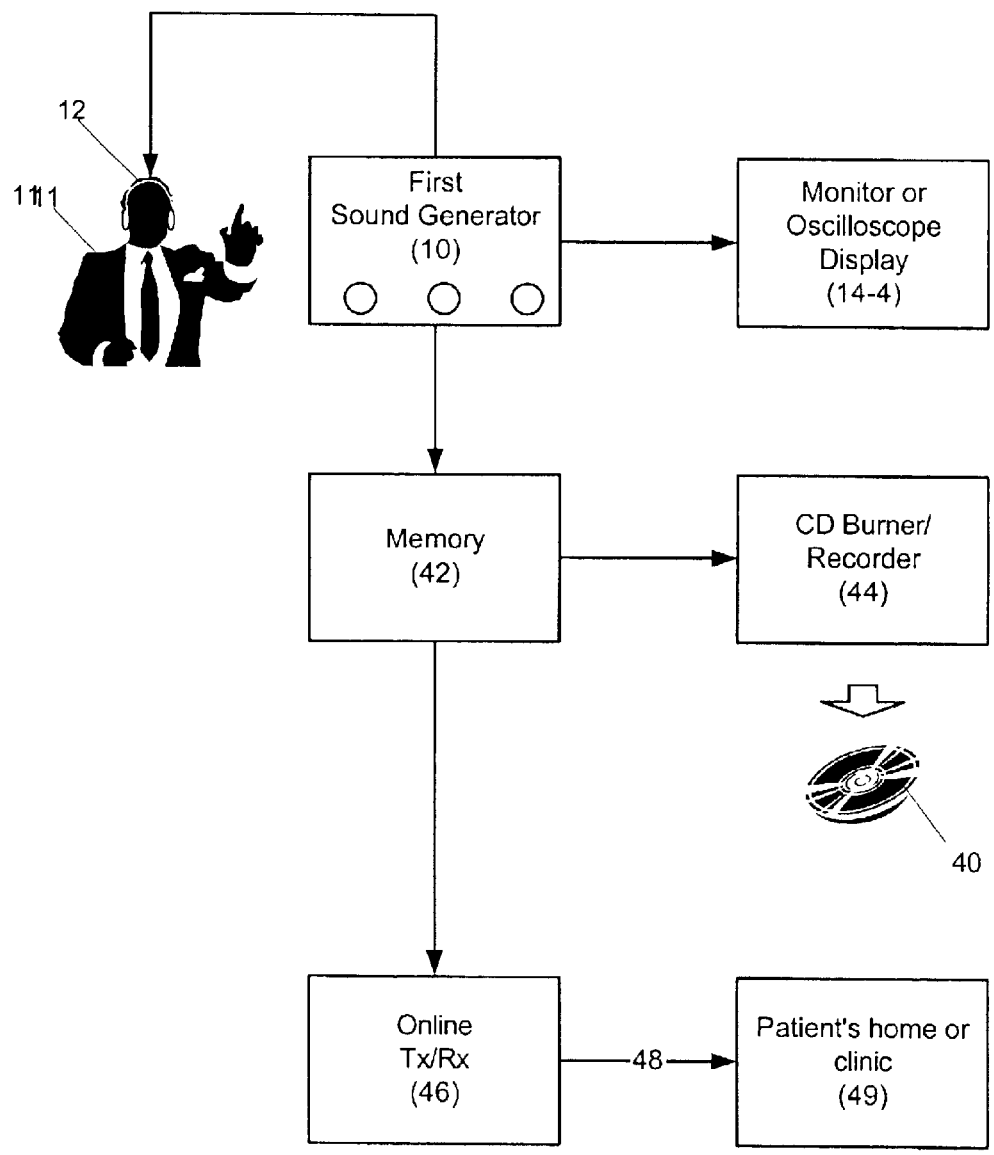
FIG. 4 is a logic block diagram illustrating another embodiment of the present invention suitable for generating a self-treatment tinnitus recording.

Referring now to FIG. 4, there is shown a logical block diagram illustrating an embodiment for preparation of a self-treatment disk 40 during a clinical treatment visit by the tinnitus patient. Sound generator 10 preferably is similar in structure and function to that described above in connection with FIG. 1. After the tinnitus patient self-typing, as described above, the appropriate phase shift of the signal from the sound generator 10 is adjusted in a series of incremental time sequenced steps to apply the incrementally phase shift treatment tone segments to the tinnitus patient via earphones 12, with the incremental phase shifts summing to at least 180 degrees or more during one treatment cycle. In the preferred embodiments, the incremental phase shifts relative to a predetermined reference may be either in six degree, 20-degree, or other increments as will be described in more detail in connection with FIG. 8.

The tinnitus treatment tone may be displayed on a monitor or oscilloscope 14-4 to enable the clinician to monitor the shift from the initial tinnitus tone f to the shifted increments of the tinnitus treatment tone $f_m$ as shown in FIG. 2. During the patient treatment protocol, audio or digital memory 42 records the audio signals of the initial tinnitus treatment tone and each of the phase-shifted increments of the tinnitus treatment tone as it is applied to the patient via headphones 12. Connected to the memory unit 42 is a CD burner or other similar audio recording device 44, which, in response to the output of the memory device 42, creates a self-treatment recording or disk 40. Alternatively, memory unit 42 is coupled to an online transmitter/receiver 46 which may comprise a web-enabled computer or server that is connected to the Internet or World Wide Web. A communication link 48 can then be established with the transmitter/receiver unit 46 via the Internet or World Wide Web. This link 48 can selectively deliver the tinnitus treatment data for a particular patient to the patient's home computer or a remote clinic 49.

Figure 5:
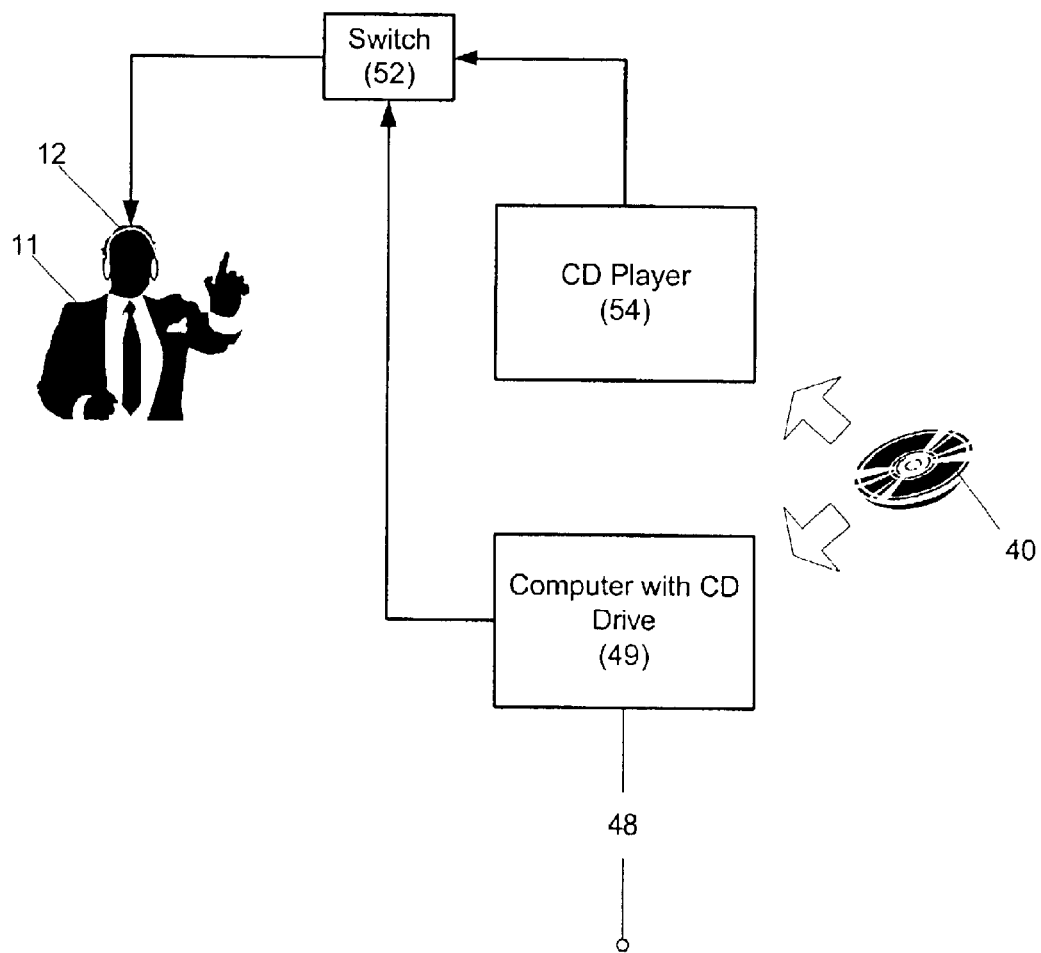
FIG. 5 illustrates another embodiment of the self-treatment tinnitus process.

Referring now to FIG. 5, an embodiment of apparatus suitable for home self-treatment system utilizable in accordance with yet another embodiment of the present invention. A tinnitus self-treatment disk 40, designed uniquely for one specific patient, is either delivered to the patient following his or her tinnitus treatment at a clinic as described above in connection with FIG. 4. Alternatively, the audio treatment data may be transmitted to the patient's home PC 49 over a connection 48 to the Internet or World Wide Web. As shown in FIG. 5, a switch 52 selectively couples the output of the PC 49 or a CD player 54 to the patient's headphones 12. Thus the patient 11 is able to utilize a self-treatment disk 40 to obtain relief from tinnitus conveniently in his or her home.

Figure 6:
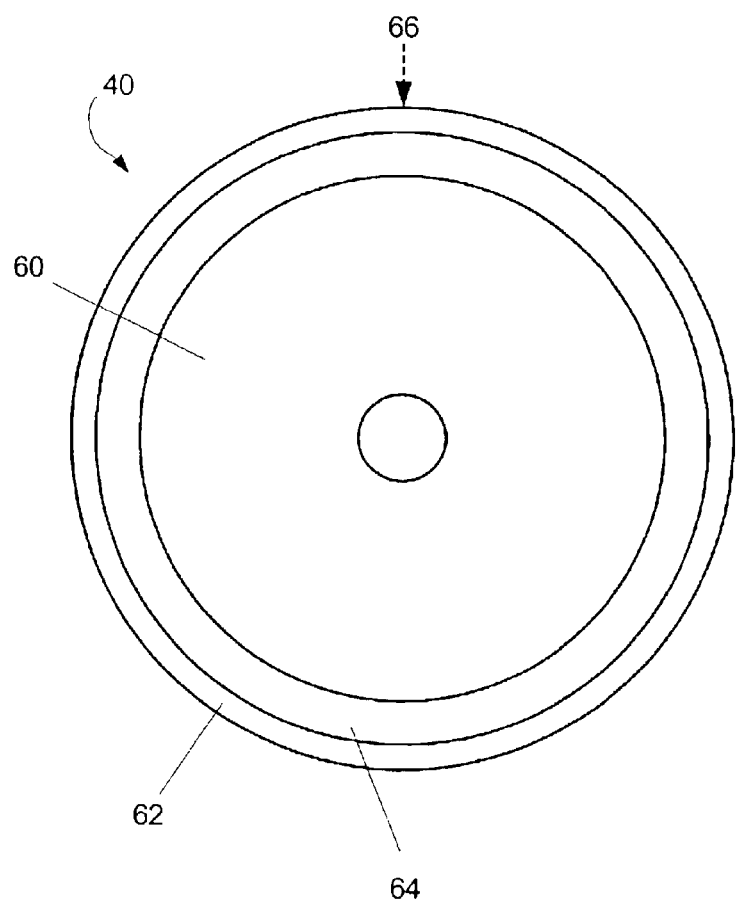
FIG. 6 illustrates an embodiment of the self-treatment recorded disk protocol of the present invention.

Referring now to FIG. 6, there is schematically shown a CD disk layout in accordance with yet another embodiment of the present invention. CD disk 40 may comprise a flat, round body 60 having a plurality of audio tracks (e.g., 62 and 64) arrayed in a generally circular pattern on at least one surface thereof. The CD disk 60 may be of any well-known type commercially available. The disk 60 will preferably have a fixed reset or start position 66. The tinnitus treatment data may be recorded on the disk 40 by any well-known audio or digital process. Similarly, the tinnitus treatment data may be stored on any other device capable of recording audio data including, but not limited to, magnetic tape, floppy or optical disk, semiconductor memory, etc. Additionally, the tinnitus treatment data may be recorded in any audio format, including, but not limited to, compact disc, MP3, wave (.wav), etc.

Figure 7:
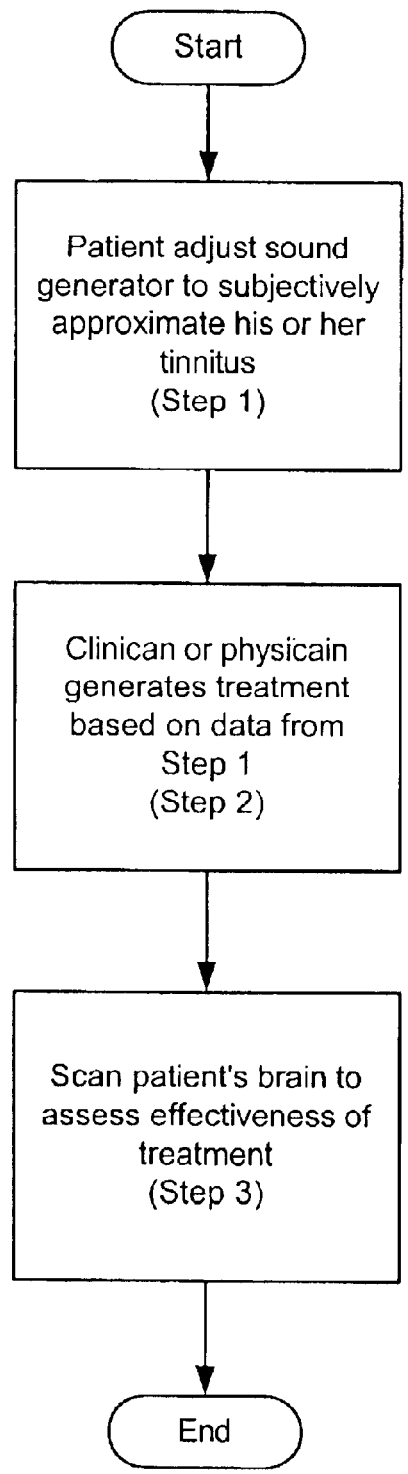
FIG. 7 illustrates a logic flow diagram for assessment of applicant's phase shift treatment protocol in accordance with embodiments of the present invention.

Referring now to FIG. 7, there is shown a logical flow diagram of an illustrative embodiment of applicant's novel process for generating objective assessment data of applicant's phase shift tinnitus treatment protocol. As hereinabove stated, applicant's treatment protocol begins with a screening of potential tinnitus patients to determine eligibility for the mono-frequency tinnitus phase-shift treatment and the initial screening may be done in accordance with MATTP or an equivalent medical protocol. In addition audiometry hearing tests may be conducted as part of, or before or after the treatment. In step 1, selected mono-frequency patients are asked to subjectively "sound-type" his/her tinnitus sound frequency utilizing, for example, an adjustable sound wave generator 10, as described above, on a blind basis to quantify his/her tinnitus tone as to frequency and amplitude. Preferably patients are asked to repeat the patient's subjective "sound typing" several times to ensure the accuracy of the patient's subjective matching of his/her tinnitus tone with the output of the frequency generator as to tone and amplitude.

Data from step 1 is utilized in step 2 by the attending clinician or physician to generate an appropriate external sine wave treatment tone substantially equal to the patient's tinnitus tone. Then, the generated treatment tone is time-shifted through a plurality of successive substantially equal predetermined step increments totaling 180 degrees whereby the generated wave form is brought through such sequential phase shifting into a series of canceling and eventually into a reciprocal canceling relationship with the patient's tinnitus tone during a treatment period or zone, as will be further described in connection with FIGS. 8 and 9 hereinafter.

In step 3, the tinnitus patient, after completing step 2, may be subjected to a PET or Functional MRI Brain Scan to objectively assess the patient's current tinnitus activity in order to objectively quantify the elimination or degree of substantial reduction in the amplitude of the patient's tinnitus tone after receiving applicant's phase shift cancellation treatments. These procedures are routinely conducted as part of many on going clinical studies. Recently Danish, Swedish and French investigators have confirmed positive PET Brain Scans in the auditory cortex of tinnitus patients. It should be noted that the Brain Scans of tinnitus patients may be conducted before, during or some time after the phase shift tinnitus treatment has been administered to gain additional objective patient treatment data for tinnitus patients.

Figure 8A:
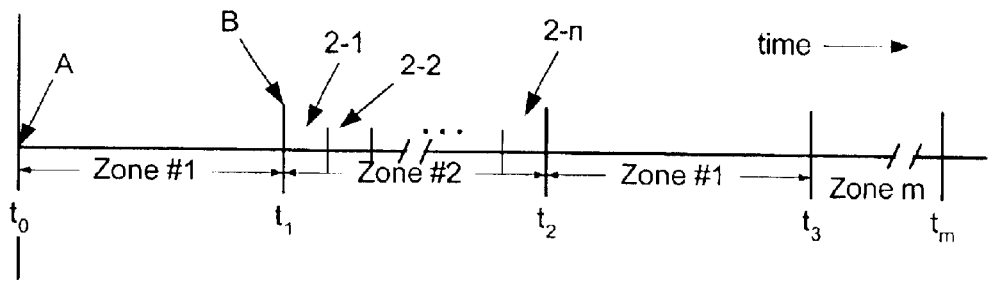
FIGS. 8A, 8B and 8C illustrate various time lines for embodiments and layouts of the sequential self-treatment protocol in accordance with embodiments of the present invention.
Figure 8B:
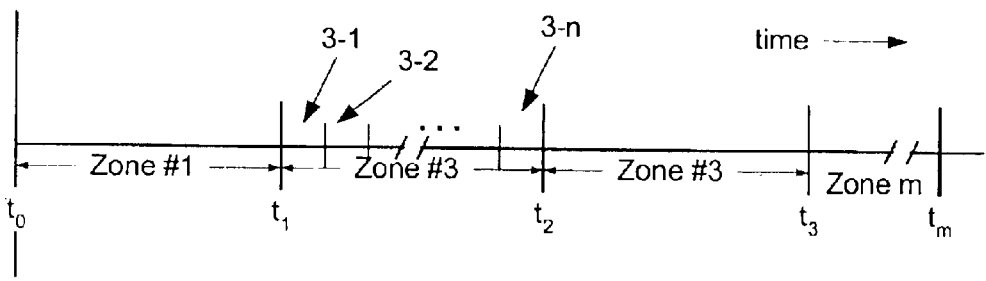
Figure 8C:
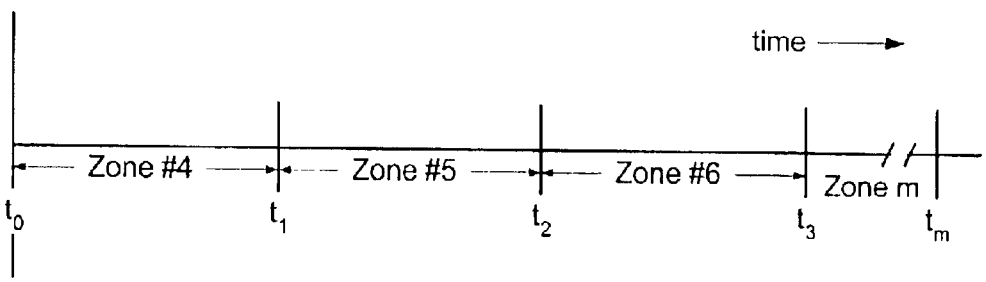

Referring now to FIGS. 8A, 8B and 8C, there is illustrated a series of time-sequence line graphs of alternate embodiments for applicant's self-treatment disk 40 layouts. Referring to FIG. 8A, a first section or zone #1 of the tinnitus treatment recording begins at point A, which preferably is the start or reset position of a designated recording track as hereinabove explained with reference to FIG. 6. The reset or start position is shown as $t_0$ on the time scale which, as shown, increases from left to right on the line graphs. Beginning at point B, there is shown a series of subdivisions of zone #2, namely 2-1, 2-2 . . . 2-n. The time duration of the subdivisions of zone #2 corresponds to the time duration of each incremental phase shift of a particular patient's protocol. As described above in connection with FIGS. 1 and 2, the number of incremental steps is selected by the attending clinician or physician for a particular patient in an appropriate manner whereby the total of the incremental steps sum to at least a 180 degrees during one treatment segment or zone. In a preferred embodiment, applicant has successfully utilized incremental phase shift steps of six degrees with each incremental step lasting a predetermined time, for example one minute. Applicant has likewise achieved favorable patient responses utilizing a series of 20-degree incremental steps with each incremental step lasting ten minutes. As shown in FIG. 8A, the first patient treatment recorded in zone #2 of the self-treatment disk 40 ends at $t_2$ and a subsequent or repeated zone #1 treatment may extend from time $t_2$ to $t_3$, etc.

Referring now to FIG. 8B, zone #1 may comprise the external tinnitus treatment tone $f_1$ as determined in the patient self-testing procedure as described above. In this embodiment, the phase shift treatment begins in zone #3 with a series of incremental phase shifts of the patient treatment tone, with the incremental shifts graphically illustrated as segments 3-1, 3-2 . . . 3-n. Another embodiment of applicant's phase shift tinnitus treatment may involve, for example, a series of nine incremental steps of 20-degree increments, with each increment lasting ten minutes for a total treatment time of 90 minutes. As shown in FIG. 8B, the initial zone #3 treatment time may be followed by a second zone #3 treatment phase identical to that immediately described above.

As shown in FIG. 8C, a patient self-treatment disk may comprise any number of treatment zones illustrated as treatment zone #4, zone #5 and zone #6. As described above, in connection with FIGS. 3A, 3B and 3C, since the instantaneous phase of a patient's internal tinnitus tone cannot be measured or determined using currently available electronic or acoustic instrumentation, there will be, in most instances, a phase offset between the patient's tinnitus tone and the externally generated patient treatment tinnitus tone. Thus in accordance with applicant's phase shift tinnitus treatment protocol a patient's treatment may be tailored in several ways by the clinician to obtain desired patient treatment responses. This may involve adjusting the number of incremental phase shift steps, e.g. 2-2 . . . or 3-2 . . . , to achieve diminution and ultimately a phase shift sequence resulting in a reciprocal canceling relationship between the externally generated tinnitus treatment tone I(t) and the patient tinnitus tone P(t) as shown in FIGS. 3A, 3B and 3C.

As is well known in the medical arts, a tinnitus condition in humans may have many different forms and many, very different causes. For a brief survey of medical tinnitus treatment literature, reference may be had to the above cross-referenced U.S. application Ser. No. 10/083,088. While there is no known "cure" for tinnitus, for those individuals who suffer substantial medical disability from tinnitus any, even temporary, relief can be very significant.

In the above cross-referenced application, application Ser. No. 10/083,088, patient clinical results from a 28 patient blind tinnitus single step 180-degree phase shift treatment protocol study are reported. In that study, seven patients (25%) experienced excellent results achieving more than 90% reduction in tinnitus loudness. 15 patients (more than 54%) experienced either "Very Good" or "Good" results having achieved temporary relief of at least a 50% reduction in tinnitus loudness. It is believed that utilizing the above-described six-degree phase shift segments protocol, for example, with each segment having a duration of at least one minute will achieve substantially improved results over the techniques described in application Ser. No. 10/083,088.

Figure 9:
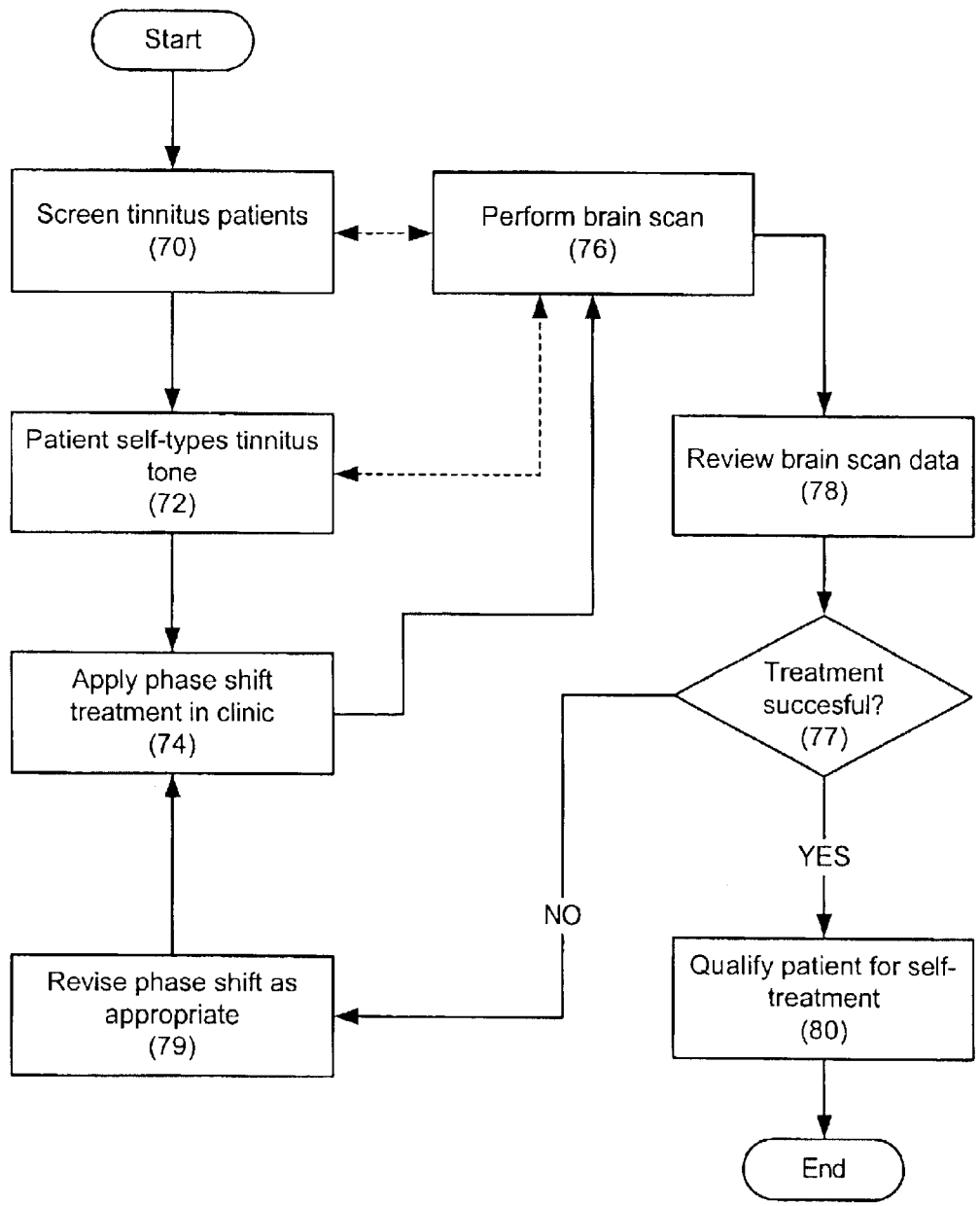
FIG. 9 is a logic block diagram illustrating various features and steps for an objective testing of applicant's phase shift tinnitus treatment protocols in accordance with embodiments of the present invention.

Referring now to FIG. 9, there is illustrated a logic block diagram for generating and utilizing objective patient data regarding the efficacy of a particular patient's phase shift tinnitus treatment protocol in accordance with other aspects of applicant's novel treatment protocol.

Block 70 illustrates the screening process for determining whether a tinnitus patient is a good candidate for the mono-frequency phase shift treatment. As stated above, medical science cannot in most instances identify the exact or likely cause of a patient's tinnitus condition nor describe the precise mechanism or mechanisms causing a particular patient's tinnitus condition.

As illustrated in block 72, if a patient exhibits mono-frequency tinnitus which, for example is not related to drug use, then the patient is asked to self type his/her tinnitus tone utilizing an externally generated tone from a sound generator wherein the externally generated tone is manipulated to match the subjectively determined patient's tinnitus tone. As stated above, the patient's self-typing process is preferably repeated several times, on a blind basis, to ensure accuracy. Thereafter, as illustrated in block 74, the patient's subjectively determined treatment tone is incrementally phase shifted through at least a full 180 degree shift in a single treatment session to thereby bring the externally generated tone into a reciprocal, wave-canceling relationship with the patient's tinnitus tone.

Following the phase shift tinnitus treatment protocol as illustrated in block 76, the patient may be subjected to a PET or MRI Brain Scan procedure to objectively determine the effect of the phase shift treatment to reduce, minimize or eliminate the brain activity in the auditory cortex normally associated with a patient's tinnitus condition. It should be noted that, as shown in FIG. 9 by the dotted lines from block 70 and block 72 to block 76, it may be desirable in some instances to perform a Brain Scan both before and after a patient has received a phase shift treatment. As shown in block 78, a medical review of the Brain Scan data obtained either before and sometime after a patient receives a phase shift tinnitus treatment may assist a clinician in altering or revising, at block 79, a phase shift treatment protocol for individual patients. Whether any such adjustment is needed is determined at block 77.

As discussed above, there is currently no medical treatment for tinnitus which "cures" a patient's tinnitus condition permanently. Thus, while a particular mono-frequency tinnitus patient experiences substantial reduction or temporary elimination of his/her tinnitus condition following an application of applicant's improved phase shift tinnitus treatment, the residual effect generally lasts only for a limited time, on the order of hours or days, or as long as ten days in a few instances. Thus, the use of the objective brain scan data may assist the clinician as shown in block 80, to classify a patient self-treatment status. As described above in connection with FIGS. 4 and 5, in accordance with another aspect of the present invention, a self-treatment disk 40 may be prepared during a clinical tinnitus treatment for certain qualifying patients thus enabling them to utilize a self-treatment disk in the convenience of their home as often as their condition necessitates such follow-up treatments.

While a number of alternative embodiments of applicant's novel apparatus and process for the treatment of tinnitus have been described, those skilled in the medical and auditory arts will recognize that the described embodiments are illustrative and additional changes or modifications of the described preferred embodiments may be made without departing from the scope of the present inventions embodied in the following claims.

The preceding description has been presented only to illustrate and describe embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A process of treating mono-frequency tinnitus patients comprising the steps of:

enabling each patient to subjectively determine his/her tinnitus tone relative to an externally generated sound wave having the same frequency and amplitude as the patient's tinnitus tone, applying to the patient via an audio transducer an externally generated sound wave having substantially the same tone and amplitude as the patient's tinnitus tone, and shifting said externally generated sound wave through a plurality of predetermined angular increments while said externally generated sound wave is applied to said patient whereby a progressive angular phase shift relationship is effected through said successive plurality of angular increments with reference to a predetermined initial point of said externally generated wave form thereby causing at least a partial cancellation or reduction in the amplitude of the patient's tinnitus tone.

2. The process of claim 1 wherein the step of shifting comprises additional steps of continuing said successive incremental shifting steps through a total of at least 180 degree angular phase shift of said external sound wave thus causing both a series of partial amplitude reductions and a reciprocal out-of-phase canceling relationship between the patient's tinnitus tone and said externally generated sound wave.

3. The process of claim 2 wherein each incremental angular phase shift step comprises a succession of substantially identical step segments which are substantially identical in angular displacement and in time duration.

4. The process of claim 2 including an additional step of having each patient maintain a daily tinnitus diary of self-assessment data of the frequency and amplitude of said patient's tinnitus tone following completion of a patient's tinnitus treatment.

5. The process of claim 2 comprising an additional step of performing a patient Brain Scan procedure to generate objective patient data to analyze the status or effectiveness of said patient tinnitus treatment.

6. The process of claim 2 comprising an additional step of electronically recording said externally generated sound wave as it is successively phase-shifted through said plurality of predetermined angular increments through at least said full 180 degree shift of said generated tinnitus treatment sound wave.

7. The process of claim 2 comprising an additional step of enabling a patient to perform a self treatment by playing a recording of said phase-shifted externally generated sound wave.

8. The process of claim 2 where the step of shifting comprises creating sequential phase shift segments having angular phase shifts in the order of six degrees to 30 degrees and each segment has a time duration in the order of one minute to 20 minutes.

9. The process of claim 3 wherein the step of shifting comprises the steps of defining each angular phase shift segment to substantially equal 6 degrees of angular shift and to define each subsequent segment equal to at least one minute of duration.

10. Improved apparatus for treating mono-frequency tinnitus patients comprising:
    a sound generator having selectable frequency and amplitude output wave controls,
    a speaker for audibly applying the output of said sound generator to a tinnitus patient whereby the patient subjectively defines his/her tinnitus tone in terms of frequency and amplitude, and
    a phase shift network for incrementally shifting the generated output wave subjectively selected by a patient to match said patient's tinnitus tone and amplitude to thereby achieve sound cancellation of said patient's tinnitus tone by selectively shifting said generated output wave form through a plurality of incremental segments totaling a 180° phase shift relative to a predetermined starting point of said generated wave.

11. The apparatus of claim 10 wherein said phase shift network comprises a manually selectable scale associated with said sound generator.

12. The apparatus of claim 10 wherein said phase shift network comprises an automatic sequencing switch.

13. The apparatus of claim 10 additionally comprising an electronic recorder for generating a record of said tinnitus treatment wave as said output of said sound generator is sequentially shifted through said plurality of predetermined angular phase shifts to achieve said reduction in cancellation effects upon said patient's tinnitus tone.

14. The improved apparatus of claim 13 wherein said generated treatment sound waves are recorded concurrent with a patient's clinical phase shift treatment whereby said recorded treatment sound sequences are available for subsequent self-treatment use by said patient.

15. The improved apparatus of claim 13 wherein said record of a patient's tinnitus treatment sound sequence comprises an electronic memory record and additionally comprises memory access means for selectively transferring said patient's tinnitus treatment sound sequence data to a removable memory.

16. The improved apparatus of claim 13 additionally comprising an online communication transmitter for selectively transferring said patient's tinnitus treatment sound sequence record to a remote location via an addressable communication link.

17. The apparatus of claim 10 wherein said phase shift network additionally comprises a calibration control to define each angular phase shift sequence to substantially equal 6 degrees of angular shift relative to a predetermined point of said generated wave form and to define the duration of each segment to substantially equal at least one minute in duration.

18. The apparatus of claim 10, wherein said speaker is incorporated into a headset worn by said patient.

19. A method of treating tinnitus comprising the steps of
    applying to the tinnitus sufferer a sound at a selected frequency,
    then applying to the tinnitus sufferer a succession of at least several additional sounds at the same frequency, each such additional sound being phase shifted with respect to the prior sound, and the sounds of the succession being spaced in phase in substantially equal phase intervals, and
    applying the sound at each of said phases for a fixed period of time;
    wherein at least nine phases are applied over at least a half wavelength at the selected frequency; and
    wherein a sound is applied every six degrees for at least a half wavelength at the selected frequency.

20. The method of claim 19 wherein the sound is applied for approximately one minute at each of said phases.

21. A method of treating tinnitus comprising the steps of
    applying to the tinnitus sufferer energy that varies substantially sinusoidally at a selected audio frequency and at a particular phase, and
    then applying to the tinnitus sufferer additional audio energy at the same frequency, first at a predetermined phase shift with respect to the particular phase, then at a succession of phases, in successive phase increments over at least about a half wavelength at the selected audio frequency;
    wherein the successive phase increments are approximately six degrees apart.

22. A method of treating tinnitus comprising the steps of
    applying to the tinnitus sufferer energy that varies substantially sinusoidally at a selected audio frequency and at a particular phase, and
    then applying to the tinnitus sufferer additional audio energy at the same frequency, first at a predetermined phase shift with respect to the particular phase, then at a succession of phases, in successive phase increments over at least about a half wavelength at the selected audio frequency;
    wherein the audio energy is recorded, and the recording is thereafter employed to apply the audio energy to the tinnitus sufferer.

23. The method of claim 22 wherein the recording is supplied to the tinnitus sufferer and thereafter self-administered by the tinnitus sufferer at selected time intervals.

24. A method of treating tinnitus comprising the steps of
    applying to the tinnitus sufferer energy that varies substantially sinusoidally at a selected audio frequency and at a particular phase;
    then applying to the tinnitus sufferer additional audio energy at the same frequency, first at a predetermined phase shift with respect to the particular phase, then at a succession of phases, in successive phase increments over at least about a half wavelength at the selected audio frequency; and performing a brain scan on the tinnitus sufferer to determine the effect of the treatment method.

* * * * *